United States Patent
May et al.

(10) Patent No.: US 6,855,106 B2
(45) Date of Patent: Feb. 15, 2005

(54) ENDOSCOPE AND CAMERA MOUNT

(75) Inventors: Kevin May, Anaheim, CA (US); Alex Vayser, Anaheim, CA (US)

(73) Assignee: Medivision, Inc., Anaheim, CA (US)

( * ) Notice: Subject to any disclaimer, the term of this patent is extended or adjusted under 35 U.S.C. 154(b) by 0 days.

(21) Appl. No.: 10/162,526

(22) Filed: Jun. 3, 2002

(65) Prior Publication Data

US 2003/0009084 A1 Jan. 9, 2003

Related U.S. Application Data (63) Continuation-in-part of application No. 09/527,499, filed on Mar. 16, 2000, now Pat. No. 6,398,724.

(51) Int. Cl.$^7$ ................................. A61B 1/04
(52) U.S. Cl. ........................ 600/112; 600/167
(58) Field of Search .................. 600/112, 163, 600/167, 168, 172; 359/822, 823, 825, 826; 348/73, 75

(56) References Cited

U.S. PATENT DOCUMENTS

| | | | |
|---|---|---|---|
| 3,804,081 A | * 4/1974 | Kinoshita et al. | 600/167 |
| 4,569,333 A | 2/1986 | Bel et al. | 600/133 |
| 4,742,818 A | 5/1988 | Hughes et al. | 600/133 |
| 4,905,668 A | 3/1990 | Ohsawa | 348/65 |
| 5,191,879 A | 3/1993 | Krauter | 600/109 |
| 5,528,432 A | 6/1996 | Donahoo | 348/66 |
| 5,575,757 A | 11/1996 | Kenedy | 600/167 |
| 5,599,278 A | 2/1997 | Hibbard | 600/133 |
| 5,702,350 A | 12/1997 | Vry et al. | 600/166 |
| 5,745,165 A | 4/1998 | Atsuta et al. | 348/65 |
| 5,797,836 A | 8/1998 | Lucey et al. | 600/109 |
| 5,846,186 A | 12/1998 | Upsher | 600/112 |
| 5,879,289 A | 3/1999 | Yarush et al. | 600/109 |
| 5,895,350 A | 4/1999 | Hori | 600/109 |
| 6,019,719 A | 2/2000 | Schulz | 600/109 |
| 6,059,721 A | * 5/2000 | Rudischhauser et al. | 600/167 |
| 6,069,651 A | 5/2000 | Tsuyuki et al. | 348/65 |
| 6,292,221 B1 | * 9/2001 | Lichtman | 348/345 |
| 6,540,668 B1 | * 4/2003 | Schulz et al. | 600/112 |

* cited by examiner

Primary Examiner—John P. Leubecker
(74) Attorney, Agent, or Firm—Crockett & Crockett; K David Crockett, Esq.

(57) ABSTRACT

An autoclavable endoscope suitable for attachment to a camera while hot. The structure of the endoscope adapted for attachment to the camera lens adapter presents a flat, co-planar proximal face, substantially devoid of grooves and crevices, and minimizes the space between the scope optics and the camera optics, thereby minimizing the volume of hot air that might be trapped between the endoscope and the camera.

24 Claims, 7 Drawing Sheets

ENDOSCOPE AND CAMERA MOUNT

This application is a continuation-in-part application of U.S. application Ser. No. 09/527,499 filed Mar. 16, 2000, now U.S. Pat. No. 6,398,724.

FIELD OF THE INVENTION

The inventions described below relate to the field of endoscopes and video-endoscopy.

BACKGROUND OF THE INVENTIONS

An endoscope is an instrument for the visual examination of the interior of a body cavity or viscus. Endoscopes have become widely utilized in surgery to permit performance of diagnostic and surgical procedures internally without the need for invasive surgical procedures. An endoscope is typically inserted through a small incision portal providing access to the body cavity. A lens at a distal end of the endoscope is positioned to receive light reflected from a site to be observed, and images of the site can be viewed remotely to conduct histological examinations and to perform closed, or endoscopic, surgery. As used herein, the term endoscope refers generically to viewing devices for remotely observing otherwise inaccessible body cavities with minimal trauma and intrusion, including but not limited to arthroscopes, colonoscopes, bronchoscopes, hysteroscopes, cystoscopes, sigmoidoscopes, laparoscopes, sinoscopes, small-joint dental scopes, ureterscopes, etc.

A typical endoscope includes an elongated flexible or rigid outer tube within which a lens system is disposed at a distal end. The image of the object being viewed by the optical system is transmitted through an optical system from the distal end to a proximal end of the tube for viewing by the user or for reception by a camera. Some endoscopes also carry fiber optic cables for illuminating the area of observation with light supplied by an external source.

Figure 1:
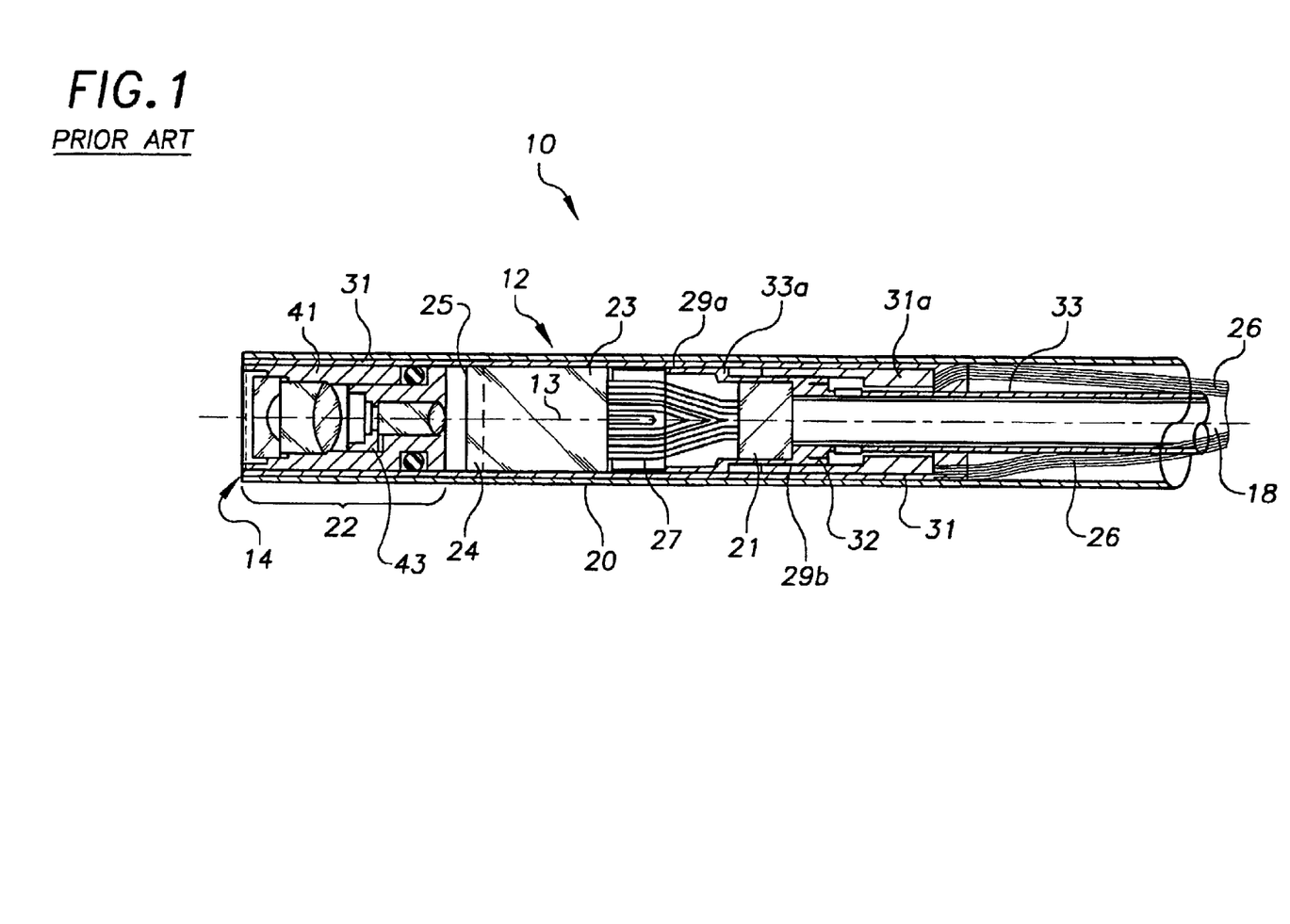
FIG. 1 is a sectional view of a distal end of a known endoscope.
Figure 2:
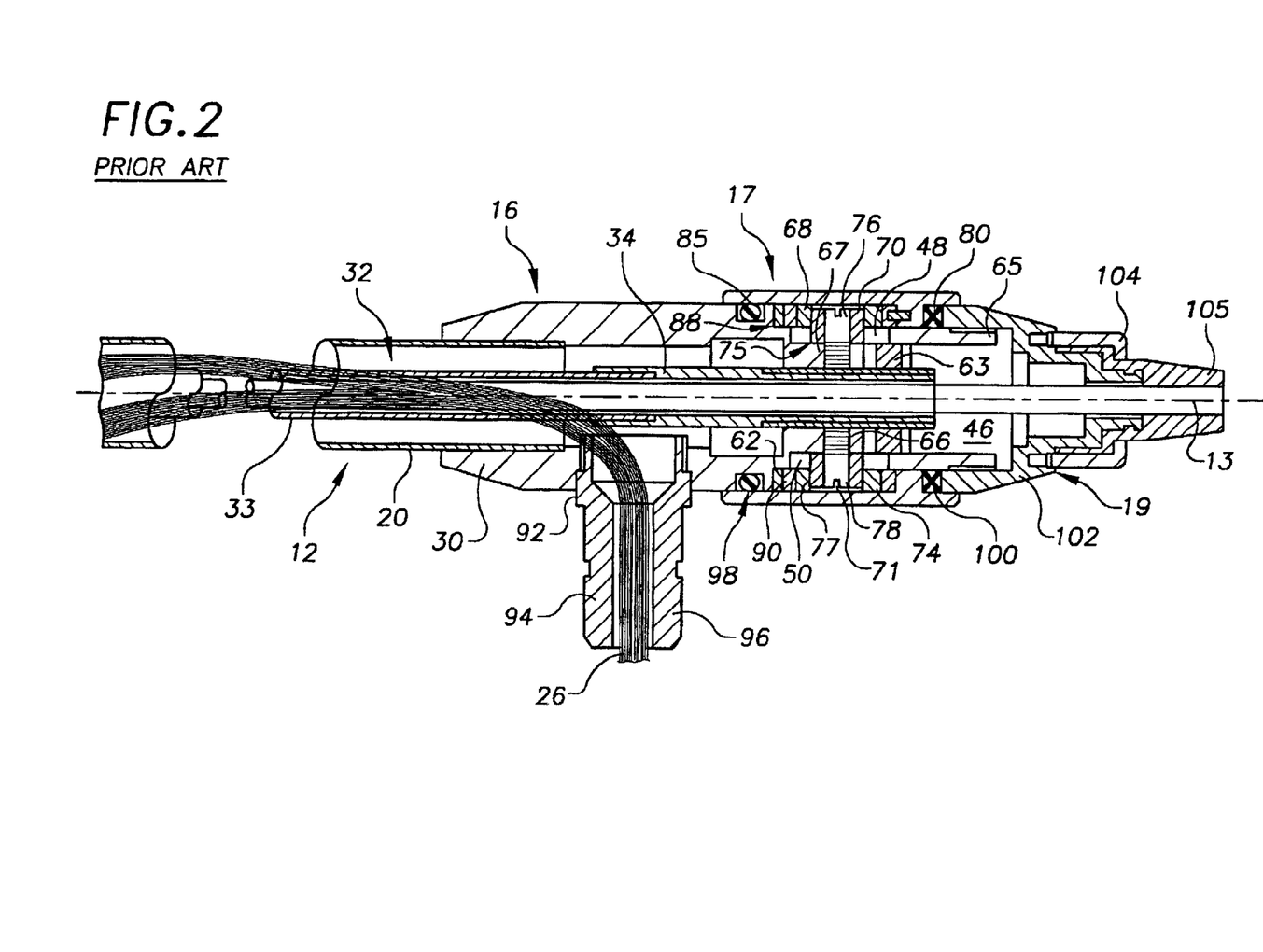
FIG. 2 is a sectional view of a proximal end of a known endoscope.

One endoscope with a typical focusing mechanism is disclosed, e.g., in Kennedy, et al., U.S. Pat. No. 5,575,757 (1996). As shown in FIGS. 1 and 2, where FIG. 1 is a sectional view of a distal end and FIG. 2 is a sectional view of a proximal end of the endoscope of U.S. Pat. No. 5,575,757. The endoscope, which is designated as a whole by reference numeral 10, includes an elongated insertion section 12 for insertion into a body cavity or narrow body passage to observe an object therein (not shown). Elongated insertion section 12 extends along a longitudinal axis 13 of endoscope 10 from a distal end 14 to a handle 16 at the proximal end 19 of endoscope 10. Handle 16 permits the user to position elongated insertion section 12 of endoscope 10 appropriately and also houses a focus control mechanism 17 for endoscope 10, which is described in detail below. A cable 18 extends from proximal end 19 for connection to a power source and camera control unit (not shown). Images observed at distal end 14 of endoscope 10 are processed by the video processor for viewing on a display unit.

Elongated insertion section 12 includes an outer tube 20 for housing an objective lens assembly 22, an image transmitting device, e.g., an electro-optic module 23, having an electro-optical sensor 24 (e.g. a charge-coupled device (CCD)) for converting optical images of the received light into electrical image signals), and light guiding fiber optic elements 26 for illuminating the area being observed. Outer tube 20 extends from distal end 14 of endoscope 10 to a first end of a main housing 30 at handle 16 where tube 20 is soldered within a counterbore of main housing 30.

Elongated insertion section 12 further includes an inner cylindrical tube 31 and a CCD tube 32, each coaxially disposed within outer tube 20. Inner cylindrical tube 31 extends from the distal end 14 of the outer tube 20 to an enlarged proximal end 31a that receives the distal end of CCD tube 32. Tube 31 is radially spaced from outer tube 20 to provide a cylindrical passage within which fiber optic elements 26 pass to distal end 14. CCD tube 32 is shown having a first cylindrical member 33 extending from a region directly behind lens assembly 22 to a region partially within main housing 30 and a second extension member 34 soldered to first cylindrical member 33 which extends to focus control mechanism 17. The distal end 33a of CCD tube 32 has a pair of enlarged diameter regions 29a, 29b as shown to receive electro-optic module 23 and a crimped end of cable 18, respectively. Electro-optic module 23 is secured into region 29a of CCD tube 32 with epoxy. Cable 18 has a woven ground conductor surrounded by a band 21, which is crimped to prove a snug fit within region 29b.

Referring to FIG. 2, focus control mechanism 17 allows a user to focus endoscope 10 by adjusting the distance between objective lens assembly 22 and CCD 24, e.g., by ±0.1 mm. As mentioned above, objective lens assembly 22 and CCD 24 are rigidly secured to inner tube 31 and CCD tube 32, respectively. The spacing between CCD 24 and lens assembly 22 is varied by moving CCD tube 32 axially along longitudinal axis 13 of endoscope 10. The front face 25 of CCD 24 is moved by focus control mechanism 17 in response to rotation of focus ring 80 by the user.

Main housing 30 has a through hole 46 extending its length to receive CCD tube 32 and to allow cable 18 to pass through endoscope 10. A pair of oblong slots 48, 50 are disposed through opposite sidewalls of an end portion 65 of main housing 30 for respectively receiving a pair of cam screws 76 and 78.

A cylindrical actuator 62 is interposed between main housing 30 and CCD tube 32 and is threaded to receive the proximal end of CCD tube 32. A pair of threaded holes 66, 67 orthogonal to axis 13 are disposed through the walls of actuator 62 and are aligned with oblong slots 48, 50 of main housing 30. A lock nut 63 secures actuator 62 to the proximal end of CCD tube 32.

Along an outer surface of main housing 30 is a cylindrical focus sleeve 68 having a pair of diametrically opposed helical grooves 70, 71 each of which is aligned with a corresponding one of threaded holes 66, 67 of actuator 62 and a corresponding one of oblong slots 48, 50. Each one of a pair of cam bearings 74 having through holes 77 engages a corresponding one of helical grooves or slots 70 and 71 and contacts actuator 62 along diametrically opposite helical surfaces of slots 70, 71.

To disassemble focus control mechanism 17, rear housing 102 is unscrewed from the rear portion of main housing 30 and with retainer 104 is drawn along cable 18. Focus ring 80 axially separated from focus sleeve 68 by applying a sufficient force proximally along the length of handle 16 sufficient to separate pin 82 from hole 85 focus sleeve 68. With focus ring 80 removed, cam screws 76, 78 are exposed and can be unscrewed from actuator 62 allowing cam bearings 74 to be removed from through holes 77 of focus sleeve 68. With cam bearings 74 removed, focus sleeve 68 can be slid off of the end of main housing 30.

Thus, by rotating focus control mechanism 17, the user shifts the front face 25 of CCD 24 relative to the objective lens assembly 22 due to interaction of the actuator 62 with helical slots 70 and 71

The endoscope of U.S. Pat. No. 5,575,757 described above is characterized by the following disadvantages. First of all, the distal end 12 of the endoscope, which is insertable into the human body has a complicated construction as it contains the entire objective optical assembly 22 and moving parts of the focusing mechanism, i.e., the image-sensing device 24. In other words, the image-sensing device 24 is an integral part of the endoscope itself. This means that the endoscope of U.S. Pat. No. 5,575,757 is inoperable as an attachment to an external image sensing device such as a CCD camera connected to a monitor. At the same time, modern clinics are normally equipped with external image sensing devices, which are widely used in practice. Furthermore, the endoscope of U.S. Pat. No. 5,575,757 has a plurality of threaded connections and seals, so that disconnection of the disposable part is a time consuming operation. The disassembly procedure is accompanied by violation of sealing conditions inside the endoscope.

The endoscope of the aforementioned construction is not autoclavable as an integral unit, as it has relatively movable inner parts. It is stated in the aforementioned patent that the insertable portion, i.e., the distal end 12, is disposable. Thus, an expensive part of the entire unit that contains objective optical assembly and the image-sensing device is disposed after the first use.

Attempts have been made to provide autoclavable endoscopes that can be sterilized without disassembling. One such construction is disclosed in Hibbard, U.S. Pat. No. 5,599,278 (1997). This autoclavable endoscope has a housing, an eyepiece, an insertion tube, proximal and distal windows, and seals that seal against the passage of contaminants into the endoscope during autoclaving. The housing, eyepiece, insertion tube, windows and light pipe are comprised of materials, which withstand a temperature of at least about 650° C. (1200° F.). However, this endoscope does not have a focusing mechanism, which is a significant disadvantage.

One of the most recent inventions in Schulz, U.S. Pat. No. 6,019,719 (2000) relates to an electronic endoscope with a semiconductor image sensor (CCD chip) for receiving the images received by an objective. The endoscope has an electronic circuit and comprises a shaft with a distal end and a proximal end, and the objective and CCD chip which are arranged at the distal end. The proximal end is held in a housing, which holds the shaft and encloses the glass-fiber optical connection. The component parts of the CCD chip unit arranged behind the objective, namely the crystal filter, JR cutoff filter and CCD chip, are arranged so as to be spaced from one another. This endoscope is autoclavable and has focusing capability performed electronically. However, this endoscope has extremely sophisticated and expensive construction that envisage insertion of the miniature visualizing device together with associated signal processing equipment into the human body.

SUMMARY

The endoscopes described below comprise sealed encapsulated optical assembly unit having no internal moveable parts and a focusing assembly combined with an external image sensing device such as a CCD camera attached to the focusing assembly for moving with the focusing assembly as an integral unit. The encapsulated optical assembly unit contains various optical elements, which receive the image from the object being observed, and transmit the obtained object to the external image sensing device. The optical system has no moving parts and therefore can be sealed and encapsulated. Thus, the optical system can be autoclaved as an integral unit without disassembling. In contrast to a conventional endoscope system in which focusing is achieved by moving elements of the optical system with respect to each other, the endoscope of the invention is focused by shifting the encapsulated optical assembly as a whole with respect to the external image sensing device.

The endoscope described below, with its camera mount and proximal window and the method by which they can be manipulated, provide for attachment of the endoscope, while hot, to a cold camera, while minimizing the degree of ensuing fogging of the lenses of the scope and camera. In some embodiments, the proximal face of the endoscope focusing tube can be manipulated to provide a smooth surface, devoid of substantial grooves, crevices and voids. The proximal window, the proximal face of the camera mount, and the seal provided between the two can be aligned in isoplanar or co-planar relationship for mounting the camera, then manipulated to move the camera mount longitudinally relative to the proximal window in order to focus the endoscope. The seal is constructed and placed to occupy substantially of the annular space between the camera mounting ring and the movable focusing tube, and has a proximal face which is flat and co-planar with the proximal face of focusing tube and the proximal face of the proximal window.

DETAILED DESCRIPTION OF THE INVENTIONS

Figure 3:
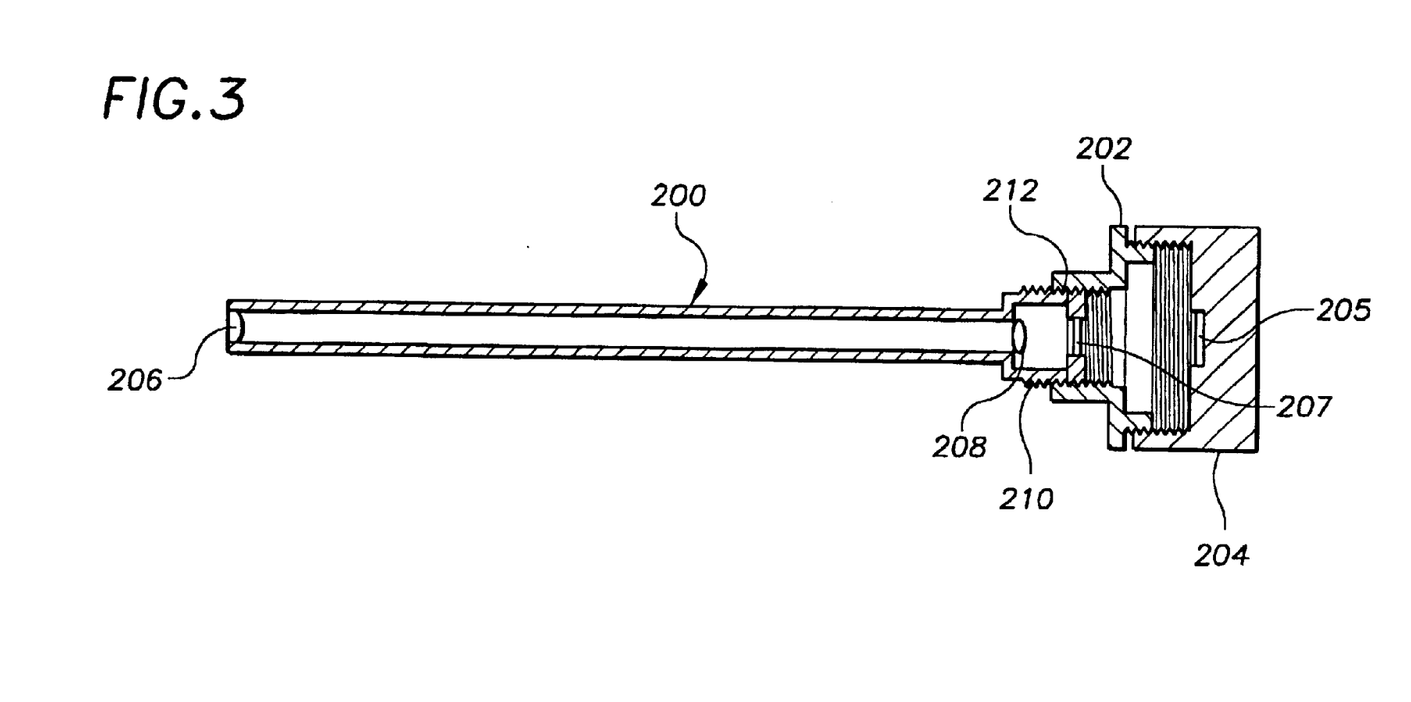
FIG. 3 is a schematic view of an endoscope made in accordance with one embodiment of the invention.

In its simplest form, the optical instrument of the invention will be described as an endoscope shown schematically in FIG. 3. It consists of two principle units having relative movement with respect to one another, i.e., a sealed encapsulated optical assembly unit 200 having no moveable parts and a focusing assembly 202 combined with an external image sensing device 204 such as a CCD camera, a still camera, or another image-receiving device attached to the focusing assembly 202 for moving with the focusing assembly as an integral unit. The encapsulated optical assembly unit 200 has an image collecting element, e.g., an objective 206 at its distal end and an image output element, e.g., an ocular 208 on its proximal end. The ocular 208 is hermetically closed with a light-permeable sealed window 207.

The external image sensing device 204 has an image-receiving plane 205 which may be the front image-receiving plane of a CCD camera. In a simplest embodiment shown in FIG. 3, the sealed encapsulated optical assembly unit 200 has an external thread 210, whereas the focusing assembly 202 has an internal thread 212 engaged with the external thread 210 so that rotation of the focusing unit 202 on the sealed encapsulated optical assembly unit 200 will change the distance Li between the ocular 208 and the image-receiving plane 205.

Thus, it has been shown that in contrast to a conventional endoscope system, in the system of the invention, focusing is achieved by shifting the encapsulated optical assembly, which has no internal moving parts, with respect to the external image sensing device. In other words, focusing can be done without changing the distance between the ocular and the relay optics.

Figure 4:
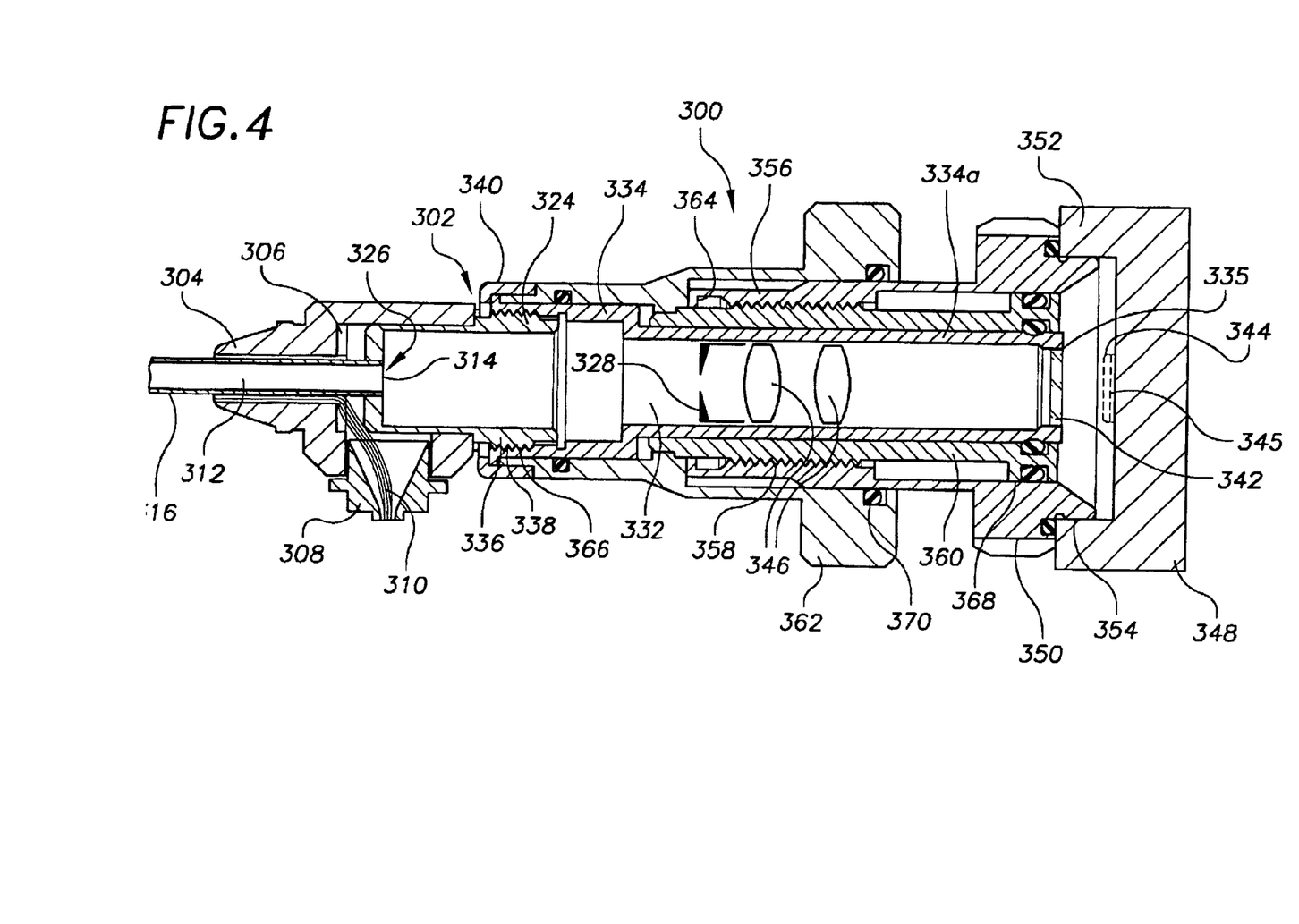
FIG. 4 is a schematic view of a proximal end of an endoscope made in accordance with another embodiment of the invention.
Figure 5:
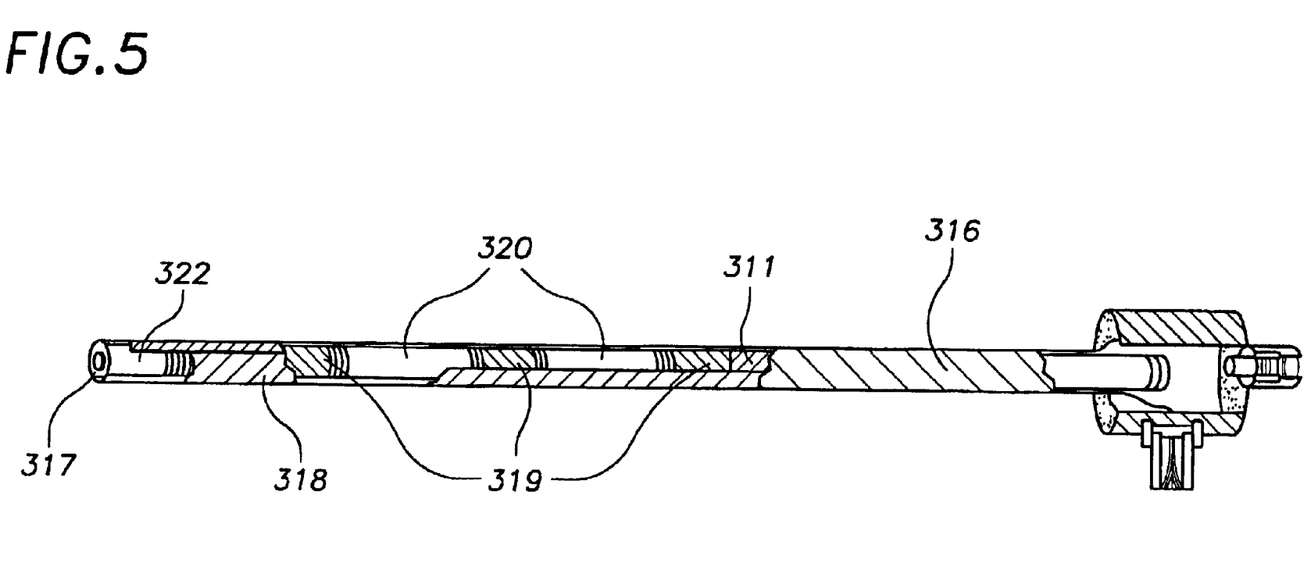
FIG. 5 is a three-dimensional view of a distal end of the endoscope of FIG. 4.

The invention will now be described in more detail with reference to a preferred embodiment shown in FIGS. 4 and 5, where FIG. 4 is a longitudinal sectional view of the endoscope, and FIG. 5 is a three-dimensional partially-broken view of a distal end of the endoscope. As shown in the drawings, the proximal end of the endoscope consists of a focusing-coupling system 300, which houses a sealed optical assembly 302. In the illustrated embodiment, the sealed optical assembly 302 consists of an insertion tube holder 304 having a cup-shaped configuration with a central hole at one end and a large-diameter bore 306 on the opposite side. A light port 308 may be formed in a sidewall of the insertion tube holder 304 for attaching a lighting device such as a fiber cable 310, which illuminates a proximal end of a light-conducting element. This is shown by reference numeral 311 in the form of braiding composed of a plurality of light-conducting optical fibers covering the entire inner surface of the insertion tube 316 (FIG. 4 and FIG. 5).

As shown in FIG. 5, the optical rod 314 is contained in an insertion tube 316 that constitutes the distal end 318 of the endoscope, which is insertable into the body of a patient. It can be seen that in the illustrated embodiment the optical rod is only one element of the sealed optical assembly 302 number of other optical elements arranged in series in the direction toward the very tip of the distal end, i.e., spacers 319, rod lenses 320, and objective 322. It is understood that all these optical elements are shown only for illustrative purposes and that the optical system may have a variety of arrangements and components, depending on a specific application of the endoscope. What is important to mention is that the interior of the insertion tube 316 is hermetically sealed. For this purpose, the end of the objective 322 which is exposed to the outside of the tube is soldered, brazed, or welded to the tube 316 with a hermetic weld seam 317. The material of the solder, as well as the materials of the optical components 314, 319, 320, 322, and of the insertion tube 316 should withstand autoclaving temperature up to 134° C. (274° F.). Examples of such materials are tin-silver solder, epoxy-type adhesive, or the like.

The proximal end of the insertion tube 316 is also soldered to the walls of the central opening 304 of the insertion tube holder 304 with a hermetic seal or weld. The proximal end of the insertion tube 316 with the optical rod 314 is further supported by a hollow eyepiece optic mount 324. For this purpose, the proximal end of the insertion tube 314 is inserted into the opening 326 of the hollow eyepiece optic mount 324 and also is hermetically sealed by soldering or welding to the walls of the opening 326. The end of the hollow eyepiece optic mount is connected to an optics barrel 334.

The front end of the optics barrel 334 has an internal thread 336 screwed onto the external thread 338 on the eyepiece optic mount 324. Sealing conditions in the threaded connection can be provided by an O-ring placed between the optics barrel 334 and the eyepiece optic mount 324 and pressed against the retaining ring 340 inserted into the annular groove in the outer surface of the eyepiece optic mount 324. Alternatively, the optics mount 324 and the optics barrel 334 can be soldered together, welded, or glued, e.g., with an epoxy adhesive, to achieve a hermetic seal.

The optics barrel 334 has an elongated small-diameter portion 334a, which extends in the direction opposite to the insertion tube 316. The rear end of the optical barrel 334 is hermetically closed by a glass plate 342, which is permeable to light. The elongated small-diameter portion 334a contains an image plate 328 which functions as a field stop and which is located in from of the image coupling system, e.g., in the form of a simple telescope 346, which is schematically shown in the form of two lenses. It is important to notice that the proximal end of the optics barrel 334 should be reliably sealed to protect the interior of this barrel from penetration of liquids and contaminants during autoclaving at temperatures as high as 650° C., though in real practice autoclaving is conducted at a temperature of about 134° C.

High resistance to temperature is achieved due to the fact the glass plate 342 has a metallized edges which allow brazing, welding, or soldering of the glass plate 342 to the rear end face of the barrel 334. The solder or welding seam 335 can be represented by tin-silver solder, or a similar material.

The image reproduced on the image plate 328 is projected through the image coupling system 346 to the image plane 344. When the endoscope is focused, this image plane 344 coincides with the front surface 345 of a CCD camera. This camera is shown schematically in FIG. 3 and is designated by reference numeral 348.

The focusing coupling system 300 is further provided with a camera adapter 350, which connects the sealed optical assembly 302 with the CCD camera 348. In the illustrated embodiment, the camera adapter 350 has threaded connection with the CCD camera, although connection of any other type, e.g., a bayonet-type connection is also possible. As shown in FIG. 4, the camera adapter 350 has an external thread 352 on its proximal end, whereas the CCD camera 348 has an internal thread 354 into which the thread 352 is screwed. The distal end of the camera adapter 350 has an internal thread 356, which is threaded onto an external thread 358 formed on the outer surface of an internal driver 360. The internal driver 360 is made in the form of a sleeve, which is slidingly fit onto the outer surface of the optics barrel. The distal end of the internal driver 360 is rigidly connected to a focus driver 362, which is made in the form of a sleeve with a flange 364. The connection between the internal driver 360 and the focus driver 362 can be made in the form of an internal thread 364 in the focus driver 362 and the external thread 366 on the distal end of internal driver 360. The focus driver 362, in turn, is rigidly connected to the optical assembly unit 302.

To avoid contamination of the internal mechanical elements of the focusing assembly 300, as well as contamination of other internal parts such as threaded portions, sliding surfaces, etc., during autoclaving under elevated temperatures of about 134° C., the connections between the part are sealed with heat-resistant seals that can withstand the above temperature. Examples of such seals are Teflon-encapsulated O-rings commercially produced by M-COR Inc., Co., Woodale, Ill.

In the embodiment shown in FIG. 4, connection between the internal driver 360 and the camera adapter 350 is sealed by an O-ring 368. Sliding fit between the focus driver 362 and the camera adapter 350 is sealed by an O-ring 370. As has been mentioned above, other seals can be made by hermetic welding, soldering, or adhesives.

Figure 6:
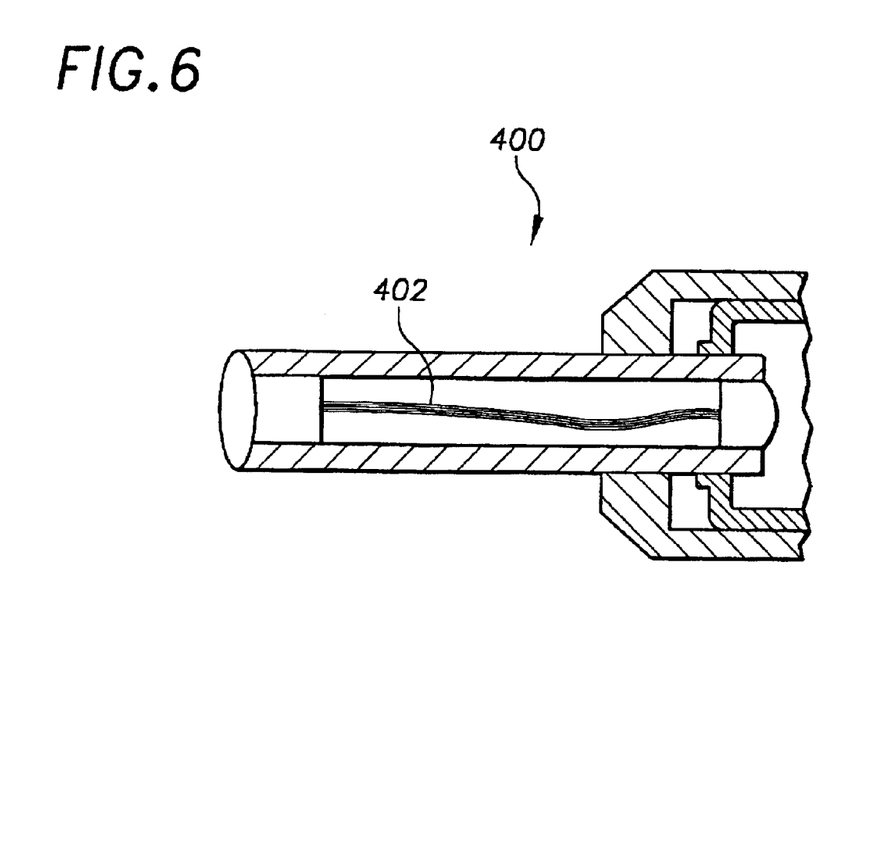
FIG. 6 is a partial sectional view of the distal end of the endoscope of the invention with an optical element in the form of an optical fiber.

FIG. 6 illustrates another embodiment of the invention which is a partial view of the distal end of an endoscope 400, which in general is the same as the one shown in FIGS. 4 and 5 and differs from it by using an optical fiber 402 instead of optical rods shown in the embodiment of FIGS. 4 and 5. The use of an optical fiber 402 is advantageous in that it allows flexibility of an insertion tube 404 which can be made of a flexible medically-acceptable material.

Figure 7:
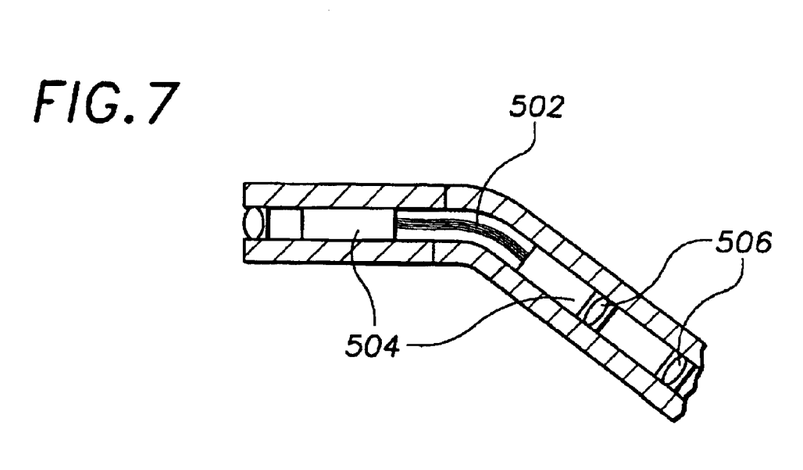
FIG. 7 is a partial sectional view of the distal end of the endoscope of the invention with an optical element comprising a combination of optical rods with optical fibers and lenses.

FIG. 7 illustrates another embodiment of the invention which is a partial view of the distal end of an endoscope 500 which in general is the same as the one shown in FIG. 6 and differs from it by using an image delivery system which combines in itself an optical fiber 502 with an optical rod 504 (or rods) and lenses 506.

In operation, the insertion tube 316 is inserted into the lumen of a human body or into the internal organ through an incision, as required by the treatment or surgery procedure. The physician then holds the focus driver 362 as a handle and adjusts the focus of the image obtained from the area of interest by rotating the camera adapter 350. This rotation changes the distance between the sealed optical assembly 302, and hence between the image plane 344 produced by the optical system, and the image receiving plane 345 of the image sensing device 348.

Upon completion of the treatment or surgery, the endoscope can be easily disconnected from the CCD camera 348 and autoclaved as a whole or partially. For partial autoclaving or for replacements of the parts, the optical assembly 302 is disconnected from the focusing unit by unscrewing the retaining ring 340 from the focus driver 362.

The focusable endoscope illustrated above is autoclavable as an integral unit, has an entirely sealed autoclavable optical assembly, has no internal moving optical components, is provided with an external focus adjustment sealed independently of the optical system, is characterized by an entirely reusable construction as a whole, has an image plane outside of the endoscope enclosure, is inexpensive to manufacture, easy to use, easy to assemble and disassemble, has an optical performance which is not affected in case of damage of the seals, and is compatible with a variety of existing external image-sensing devices.

After sterilization, it may take some time for the endoscope to cool to room temperature. The camera which is used with the endoscope may not be sterilized, or, if sterilized, is sterilized using methods, such as the Steris System 1, which leave the camera cooler than autoclaving would. If the surgeon performing the surgery or inspection attaches a hot scope to a cold camera, any moisture trapped within voids and crevices in fluid communication with the space between the scope camera mount and the camera will condense and fog the camera lens and the scope camera window. The fogging will dissipate as the scope cools, or may be avoided if the surgeon wants to wait for the endoscope to cool before mounting the camera, but this wastes expensive operating room time.

Figure 8:
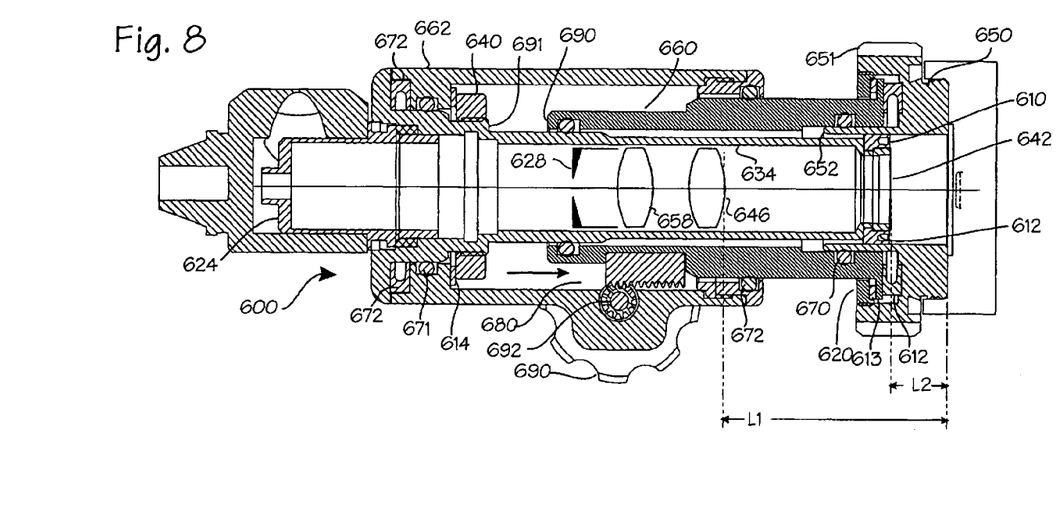
FIGS. 8 and 8a are cross sections of the endoscope with a co-planar proximal face.
Figure 8A:
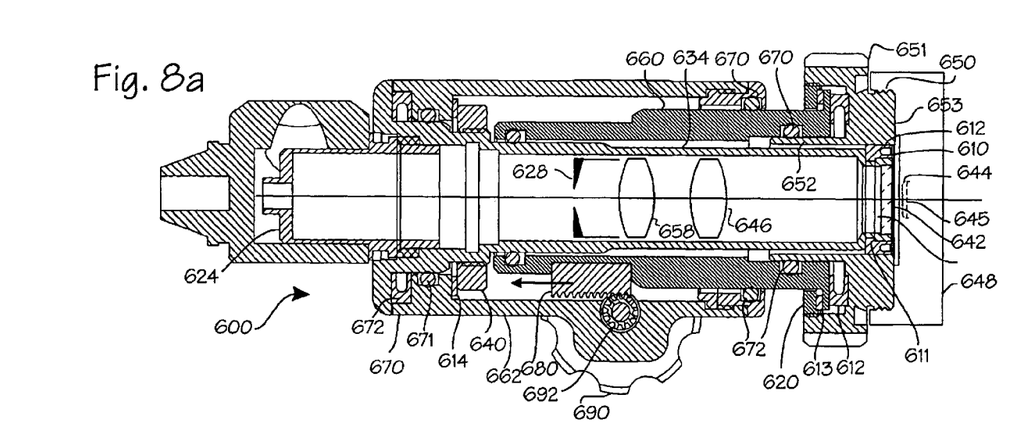

FIGS. 8a and 8 are cross sections of the endoscope with a co-planar proximal face. This embodiment minimizes the space between the camera and the endoscope, bounded by the camera mount and the camera lens adapter, and also eliminates crevices and grooves which may hold hot moist air, thereby substantially eliminating the incidence of fogging described above. The focus coupling system is constructed so that the optics barrel and the camera mount have flat proximal faces, and the optics barrel may be moved relative to the camera mount so that the proximal face of the optics barrel lies in the same plane as the proximal face of the camera mount. The construction is illustrated together with a rack and pinion focus drive mechanism, although it can also be adapted for use in the mechanism of FIG. 4.

As illustrated, the optics barrel is co-planar with the camera mount when it is moved to its most proximal position relative to the camera mount. This requires that the camera mount itself have a flat proximal face and that any seal between the camera mount and the optics barrel be coplanar with the proximal face. These features are shown in FIG. 8, which shows the focusing mechanism 600 with the optics barrel 634, slidable internal extending barrel 660, and focus driver 662 which are operable together to move the internal extending barrel 660 longitudinally relative to the optics mount 624, the optics barrel and the sealed optics assembly attached to the optics mount. The image plate 628 and imaging coupling lens 646 are disposed within the optics barrel, and fixed within the optics barrel (similar to those shown in FIG. 4). The camera adapter 650 is a proximal extension of the internal extending barrel. It is rotatable but longitudinally fixed relative to the internal extending barrel 660, as are the comparable components 350 and 360 in FIG. 3. The camera adapter has external screw threads sized and dimensioned to fit standard video camera lens adapters with matching internal threads. It is also provided with a grasping boss or flange 651 and a proximally extending barrel 652 which extends proximally into an annular space between proximal portions of the optics barrel 634 and the internal extending barrel 660. The grasping bosses are used to rotate the camera adapter relative to the remainder of the endoscope to facilitate attachment to the camera lens adapter 648. (The camera adapter may be made integrally with the internal driver, if the internal driver is rotatable or if ability to rotate is not necessary.) The portion of the camera mount that extends into the camera lens adapter 648 (on the camera) has a flat proximal face labeled as item 653. The camera adapter 650 is rotatable and longitudinally fixed to the internal extending barrel, which itself is slidable relative to the optics barrel 634, as are the comparable components 350, 360 and 334 in FIG. 4.

The optics barrel 634 is fixed longitudinally to the optics mount 624 and the focus driver barrel 662. The seal 610 provided between the proximal end of the optics barrel and the inside of the camera mount is an energized ring seal having a flat proximal surface which lies in the same plane as the proximal window 642 of the optics barrel. The ring has a substantially rectangular radial cross section (the cross section seen when the ring is cut along a radial line segment, from the proximal end to the distal end) as can be seen in the longitudinal cross section of the entire device. The ring also has an inwardly extending flange 611 disposed along the distal inner end of the ring, and is "energized" by a metal ring of u-shaped radial cross section 612 (it may also be energized with a coiled spring or other energizing means). The seal 610 is longitudinally fixed to the optics barrel, and slides with it during longitudinal translation of the optics barrel, but may be provided in a form that is fixed instead to the internal extending barrel and camera adapter assembly. This construction minimizes the space between the scope optics and the camera optics when the camera is mounted, thereby minimizing the volume of hot air that might be trapped between the endoscope and the camera.

The internal extending barrel 660 is driven by a rack and opinion drive including the pinion knob 690, pinion gear 692, and a rack or toothed bar 680 with teeth sized and dimensioned to engage the teeth of the pinion gear. The rack is disposed within the annular space between the internal extending barrel and the focus driver 662, and is fixed to the internal extending barrel. With this construction, the internal extending barrel may be driven distally and proximally relative to the optics barrel and other components of the endoscope, and this may be performed by the surgeon using a single hand. As illustrated, the proximal-most movement of the internal drive will place the window 642 in the same plane (perpendicular to the long axis of the device) as the flat proximal face 653 of the camera adapter. This is accomplished by sizing and placing the various components relative to each other such that when the rack is driven to its distal-most position, the internal drive and camera adapter are moved distally until the distal shoulder 690 meets the drive limiting shoulder or boss 691, which is formed and disposed to act as a stop at the appropriate location given the length of the internal driver. After the camera is attached, operation of the focus driver will result in longitudinal translation of the optics barrel relative to the camera, camera lens adapter and the imaging plane 644 of the camera. The screw driven focus mechanism of FIG. 4 may also be employed in an endoscope having the coplanar proximal faces illustrated in FIG. 8 and 8*a,* and endoscopes employing these or any other means for adjusting the focus, or longitudinally translating the internal extending barrel relative to the optics barrel, such as a thumb slide or a mere slidable friction fit between the barrels, may benefit from the co-planar arrangement of the proximal faces.

Various seals throughout the assembly permit rotation and longitudinal sliding of the various components while precluding entry of moisture during autoclaving. An energized o-ring, lip seal or radius seal 612 and metal ring 620 seal the camera mount to the internal extending barrel. Seals 670, 671, and 672 prevent entry of moisture into the focus driver 662 during autoclaving. Bushings 613 and 614 provide wear surfaces for the rotating components.

In use, the camera mount is screwed into the camera lens adapter. If the endoscope is hot relative to the camera (for example, if it has been sterilized immediately before use), the surgeon may operate the focus drive mechanism to move the optics barrel proximally, so that the flat, planar proximal faces of the window, seal and camera mount all lie in the same radial plane along the longitudinal axis of the device. This is illustrated in FIG. 8*a.* The surgeon may then attach the camera, and the front face of the camera optics will lie close to the overall flat surface presented by the endoscope, creating a small space between the camera optics and the endoscope optics. This small space is devoid of crevices and other reservoirs of hot, moist air remaining from autoclaving, and the space is so small as to prevent fogging in all circumstances yet encountered. After attachment, the surgeon may operate the focus drive mechanism to force the optics barrel to move distally, as necessary to adjust the distance Li between the ocular lens 646 of the optical assembly and the camera imaging plane (and, correspondingly, the distance L2 between the proximal window and the camera imaging plane).

Although the endoscopes have been shown and described in detail with reference to specific practical examples, it is understood that these examples were given only for illustrative purposes and that the materials, shapes, configurations, and structural elements of the parts and units can be changed, provided these changes do not depart from the scope of the appended patent claims. For example, in the screw driven embodiments, the physician may hold the CCD camera and focus the endoscope by rotating the driver, or rotate the endoscope while holding the driver. In all embodiments, the focus drive mechanism is most conveniently and inexpensively provided in a form which is manually operated, but these focus drive mechanisms may be motorized and automated. The endoscope and focusing assembly may also be provided in modular form, for example, by providing a coupling mechanism to the distal end of a focusing assembly to provide for coupling to an eyepiece of a conventional scope. Although the focusable optical instruments are shown and described with reference to an endoscope, the principle of the inventions are applicable to optical devices of other type such as a boroscope, veterinarian scope, etc.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. An endoscope for use in combination with a video camera having an imaging plane, said endoscope comprising:
   a sealed optical assembly (634) having a proximal end and a distal end;
   an objective lens (206) disposed within the distal end of the optical assembly;
   an ocular lens (646) disposed within the proximal end of the optical assembly;
   a focusing assembly (600) disposed on the proximal end of the sealed optical assembly, said focusing assembly comprising a first barrel (662) longitudinally fixed relative to the optical assembly and a second barrel (660), said second barrel being longitudinally moveable relative to the first barrel;
   an optical window (642) disposed within the proximal end of the sealed optical assembly, said optical window being substantially flat and establishing a substantially planar proximal face on the sealed optical assembly, said planar proximal face lying in a plane perpendicular to the longitudinal axis of the endoscope;
   a camera mount (650) extending proximally from the second barrel and longitudinally fixed thereto, said camera mount adapted for releasable connection to the video camera, said camera mount having a substantially planar proximal face, said planar proximal face lying in a plane perpendicular to the longitudinal axis of the endoscope;
   wherein the focusing assembly is operable to translate the second barrel and camera mount longitudinally relative to the sealed optical assembly such that the proximal face of the optical assembly is co-planar with the proximal face of the camera mount, and also to translate the camera mount longitudinally relative to the sealed optical assembly to focus the endoscope image on the imaging plane of the camera.

2. The endoscope of claim 1 further comprising:
   a ring seal (610) disposed between the sealed optical assembly (634) and the camera mount (650), said ring seal being longitudinally fixed to the optics assembly, said ring seal having a substantially planar proximal face which is substantially coplanar with the planar proximal face of the sealed optical assembly.

3. The endoscope of claim 2 wherein the ring seal (610) is an energized ring seal.

4. The endoscope of claim 2 wherein the ring seal (610) further comprises an inwardly extending flange (611) disposed within the distal end of the ring seal, said flange also being disposed within a circumferential groove disposed within the outer surface of the sealed optical assembly (634), thereby securing the ring seal in longitudinally fixed relationship with the sealed optical assembly.

5. The endoscope of claim 1 wherein the focusing assembly further comprises:
   a rack and pinion assembly operably connecting the first barrel and the second barrel, said rack and pinion assembly operable to translate the first barrel and second barrel relative to each other.

6. The endoscope of claim 1 wherein the focusing assembly further comprises:
   a screw driven focusing mechanism connecting the first barrel and the second barrel, said screw driven focusing mechanism comprising a threaded connection between the first barrel and second barrel, said screw driven focusing mechanism operable to translate the first barrel and second barrel relative to each other.

7. The endoscope of claim 1 wherein the focusing assembly further comprises:
   means for longitudinally translating the first barrel relative to the second barrel.

8. The endoscope of claim 1 wherein the camera mount is rotatable relative to the second barrel.

9. The endoscope of claim 1 wherein the camera mount is integrally formed with the second barrel.

10. The endoscope of claim 1 wherein the camera mount is non-rotatable relative to the second barrel.

11. The endoscope of claim 1, further comprising:
    a stop located in fixed relationship to the optical assembly, in obstructing relationship to the second barrel, wherein the second barrel is sized and dimensioned relative to the first barrel and the stop such that, when the second barrel is moved distally into contact with the stop, the proximal face of the second barrel is aligned with the proximal face of the optical assembly.

12. The endoscope of claim 1 further comprising:
    a ring seal (610) disposed between the optics assembly (634) and the camera mount (650), said ring seal being longitudinally fixed to the optics assembly.

13. An endoscope for use in combination with a video camera having an imaging plane, said endoscope comprising:
    a sealed optical assembly (634) having a proximal end and a distal end;
    an objective lens (206) disposed within the distal end of the optical assembly;
    an ocular lens (646) disposed within the proximal end of the optical assembly;
    a focusing assembly (600) disposed on the proximal end of the sealed optical assembly, said focusing assembly comprising an outer barrel (662) longitudinally fixed relative to the optical assembly and an internal extending barrel (660), said internal extending barrel being longitudinally moveable relative to the outer barrel;
    an optical window (642) disposed within the proximal end of the sealed optical assembly, said optical window being substantially flat and establishing a substantially planar proximal face on the sealed optical assembly, said planar proximal face lying in a plane perpendicular to the longitudinal axis of the endoscope;
    a camera mount (650) extending proximally from the internal extending barrel and longitudinally fixed thereto, said camera mount adapted for releasable connection to the video camera, said camera mount having a substantially planar proximal face, said planar proximal face lying in a plane perpendicular to the longitudinal axis of the endoscope;
    wherein the focusing assembly is operable to translate the inner extending barrel and camera mount longitudinally relative to the sealed optical assembly such that the proximal face of the optical assembly is co-planar with the proximal face of the camera mount, and also to translate the inner extending barrel and camera mount longitudinally relative to the sealed optical assembly to focus the endoscope image on the imaging plane of the camera.

14. The endoscope of claim 13 further comprising:
    a ring seal (610) disposed between the sealed optical assembly (634) and the camera mount (650), said ring seal being longitudinally fixed to the sealed optical assembly, said ring seal having a substantially planar proximal face which is substantially coplanar with the planar proximal face of the sealed optical assembly.

15. The endoscope of claim 14 wherein the ring seal (610) is an energized ring seal.

16. The endoscope of claim 14 wherein the ring seal (610) further comprises an inwardly extending flange (611) disposed within the distal end of the ring seal said flange also being disposed within a circumferential groove disposed within the outer surface of the sealed optical assembly (634), thereby securing the ring seal in longitudinally fixed relationship with the sealed optical assembly.

17. The endoscope of 13 claim wherein the focusing assembly further comprises:
    a rack and pinion assembly operably connecting the outer barrel and the inner extending barrel, said rack and pinion assembly operable to translate the outer barrel and inner extending barrel relative to each other.

18. The endoscope of claim 13 wherein the focusing assembly further comprises:
    a screw driven focusing mechanism connecting the outer barrel and the inner extending barrel, said screw driven focusing mechanism comprising a threaded connection between the outer barrel and inner extending barrel, said screw driven focusing mechanism operable to translate the outer barrel and inner extending barrel relative to each other.

19. The endoscope of claim 13 wherein the focusing assembly further comprises:
    means for longitudinally translating the outer barrel relative to the inner extending barrel.

20. The endoscope of claim 13 wherein the camera mount is rotatable relative to the inner extending barrel.

21. The endoscope of claim 13 wherein the camera mount is integrally formed with the inner extending barrel.

22. The endoscope of claim 13 wherein the camera mount is non-rotatable relative to the inner extending barrel.

23. The endoscope of claim 13, further comprising:
    a stop located in fixed relationship to the optical assembly, in obstructing relationship to the inner extending barrel, wherein the inner extending barrel is sized and dimensioned relative to the outer barrel and the stop such that, when the inner extending barrel is moved distally into contact with the stop, the proximal face of the inner extending barrel is aligned with the proximal face of the optical assembly.

24. The endoscope of claim 13 further comprising:
    a ring seal (610) disposed between the optics assembly (634) and the camera mount (650), said ring seal being longitudinally fixed to the optics assembly.

* * * * *